United States Patent
Pameijer et al.

(10) Patent No.: US 6,547,566 B2
(45) Date of Patent: Apr. 15, 2003

(54) METHOD FOR REMOVAL OF DENTAL CEMENT

(75) Inventors: Cornelis Pameijer, Simsbury, CT (US); Daniel Fortin, Verdun (CA); Steven R. Jefferies, York, PA (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/779,217

(22) Filed: Feb. 8, 2001

(65) Prior Publication Data

US 2001/0031447 A1 Oct. 18, 2001

Related U.S. Application Data

(60) Provisional application No. 60/181,042, filed on Feb. 8, 2000.

(51) Int. Cl.$^7$ ............................................. A61C 5/04
(52) U.S. Cl. .................................................. 433/226
(58) Field of Search ................................ 433/215, 217, 433/219, 226, 220

(56) References Cited

U.S. PATENT DOCUMENTS

| | | | | | |
|---|---|---|---|---|---|
| 4,650,550 | A | * | 3/1987 | Milnes et al. ............... | 433/215 |
| 6,186,792 | B1 | * | 2/2001 | Discko ........................ | 433/220 |
| 6,191,190 | B1 | * | 2/2001 | Blackwell et al. .......... | 433/215 |
| 6,313,191 | B1 | * | 11/2001 | Blackwell ................... | 433/217 |
| 6,315,567 | B1 | * | 11/2001 | Hasel ......................... | 433/226 |

OTHER PUBLICATIONS

Iglesias et al; Journal of Prosthodontics, vol. 5, No. 3 (Sep. 1996, pp 201–205; Accuracy of Wax, Autopolymerized and Light–Polymerized Resin Pattern Materials.

Keyf et al; Journal of Oral Rehabiliation, 1994 vol. 21, pp. 367–371, No. 4, Jul.; "The effect or margin design on the marginal adaptation of temporary crowns".
Byrne et al; The Journal of Prosthetic Dentistry; Mar. 1986; vol. 55, No. 3; "Casting accuracy of high–palladium alloys".
McLean et al; Br. Dent. J. vol. 131; Aug. 3, 1971; "The estimation of Cement Film Thickness by an In vivo technique".
Lang et al; Journal of Clinical Peridontology 12983; 10; 563–578, No. 5 Sep.; "Clinical and microgiological effects of subgingival restoations with overhanging or clinically perfect margins".
Pameijer et al; Scanning Election Microscopy 1983 (Part III); Proceeding of the Workshop on Scanning Electron Microscopy in Pathology; pp. 357–364; "Three Replica Techniques for Biological Specimen Preparation".
Pameijer et al; Operative Dentistry; General Dentistry; Nov.–Dec. 1996; Retentive properties and film thickness of the 18 luting agents and systems; pp. 524–530.
Quintessence International Editorial; William F. Wathen, DMD; "Do you practice marginal dentistry?" p. 683.
Soderholm et al; General Dentistry; Jul.–Aug. 1996; "Factors affecting reliability of a resin–based cement joint".

* cited by examiner

*Primary Examiner*—Todd E. Manahan
(74) *Attorney, Agent, or Firm*—Douglas J. Hura; James B. Bieber

(57) ABSTRACT

A method of restoring a tooth using a dental construct of the type wherein the construct is placed onto the tooth using a dental cement to bond the construct to the tooth. After placement of the construct onto the tooth, excess cement is removed with a soft, pointed brush. The dental margins are then brushed with a photocurable dental resin cement which is the same as or different from the dental cement used to bond the construct to the tooth. The resin cement is then light cured.

1 Claim, 4 Drawing Sheets

METHOD FOR REMOVAL OF DENTAL CEMENT

This application claims the benefit of Provisional application Ser. No. 60/181,042, filed Feb. 8, 2000.

BACKGROUND OF THE INVENTION

The fabrication of cast restorations involves numerous technique-sensitive procedures for the attainment of accurately fitting restorations. Marginal fit has been identified as a cause of failure of cast restorations. Accurate marginal fit and proper contour and surface finish of a crown are critical to maintain a healthy contiguous gingiva.

Unsealed margins can potentially be an entry point for microorganisms, resulting in accumulation of acids and debris, leading inevitably to recurrent caries. A resin-based cement, that is less soluble in the mouth than most other cements, can achieve such a seal. With the use of these newer resin-based and resin ionomer cements, removal of excess material extruding from margins after placement of dental constructs such as crowns, inlays, onlays or veneers, can be difficult and often incomplete when the cement is allowed to polymerize completely, since at that stage they are extremely hard. Especially access to interproximal surfaces is difficult, potentially leaving practically insoluble remnants of cement in areas that are difficult to clean and therefore prone to periodontal disease. When using resin or resin ionomer cements it is therefore beneficial to the practitioner to remove the cement before it sets, or during the gel or initial setting phase, making this step an easier and more predictable procedure. It was speculated that the technique of cement removal has a direct effect on the marginal configuration and seal of the interface preparation/restoration.

TECHNICAL FIELD

The present invention provides a technique for the removal of resin or resin ionomer dental cements that yields improved marginal adaptation and a good marginal seal. Ideal or acceptable margins were defined as margins being continuous with the emergence profile of tooth and restoration. In addition dye penetration followed by sectioning of cemented restorations was used to evaluate the quality of the marginal seal.

PREFERRED EMBODIMENTS FOR CARRYING OUT THE INVENTION

Fabrication of Castings

Figure 1:
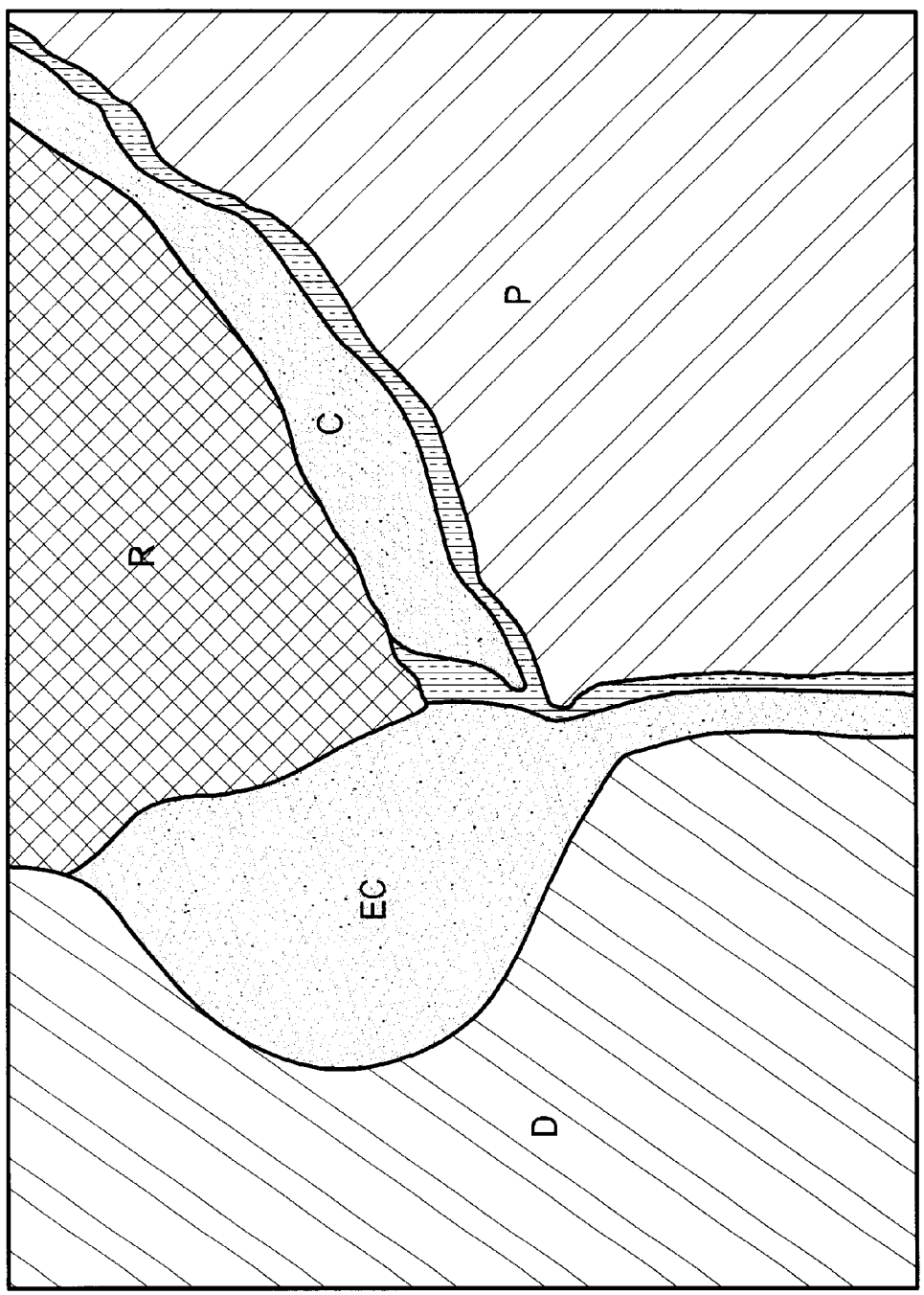
FIG. 1. Field Emission Scanning Electronic Micrograph (FESEM) of a representative sample of Group 1. The cement (C) is closely adapted to the metal casting but separated from the balloon shaped excess cement (EC) by a space caused by a shrinkage artifact. There is also a shrinkage artifact between the cement and the preparation (P). Preparation, excess cement and restoration are surrounded by duralay (D) in which the teeth were imbedded to allow for sectioning FIG. 2. An example of group 2. The cement does not reach the crown margin (M) and is short of a distance of at least 100 m$\mu$. The cement (C) broke off within the crown margin between restoration (R) and preparation (P).

Extracted intact human teeth were prepared free hand to full crown preparations with a chamfer finish line and an angle of convergence of ±10–12 degrees using chamfer diamond burs (Ultradent Products Inc. South Jordan, Utah). Upon completion of the preparations the roots were imbedded in a block of plaster leaving the CE-junction 2–3 mm above the plaster. Impressions were made of the preparations using, an addition vinyl polysiloxane material (Reprosil, L. D. Caulk & Co. Milford, Del.) and poured in die stone (Die stone, Heraeus Kulzer, NY, N.Y.). The teeth were stored in water at room temperature when not used. The dies were trimmed to the margins, painted with a die spacer (Belle de St. Claire, Chatsworth, Calif.) of ±25 $\mu$m and direct wax patterns fabricated. Using routine investing and casting techniques, the wax patterns were cast in Type III gold (Jensen, Wallingford, Conn.). If necessary, adjustments of the internal fitting surface of the castings were made until well fitting, clinically acceptable castings were available on the original teeth. Three castings per group for one of five cement removal techniques were available for analysis. The cement used for cementation was a dual-cure resin cement, Calibra (Dentsply/Caulk Div. Milford, Del.).). According to manufacturer's instructions equal lengths of base and catalyst (low viscosity, light shade) were extruded on a paper pad and mixing was accomplished within 10 s achieving a uniform color. The cement was loaded in the casting, seated on the preparation and held firmly in place for 10 s. If light curing was part of the protocol a Max-Light (Dentsply/Caulk Div.) with an output of 320 mw/cm2 was used. When not worked on the samples were stored in water at room temperature. The following five techniques were analyzed:

Group 1. The cement that extruded at the margins was light cured for 8–10 s per surface (buccal, mesial, distal and lingual) and removed immediately with a curette (Hu-Friedy, universal curette). After 8–10 seconds light curing the cement had reached a gel phase facilitating its removal. The cement was then allowed to polymerize completely for an additional 8 minutes before being stored in water.

Group 2. Excess cement was light cured for 30 s per surface and the margins scaled after 10 minutes storage on the bench, when complete polymerization had taken place.

Group 3. Excess cement was removed immediately after seating the restoration with a soft pointed camel hairbrush. The margins were then brushed with Probond Bonding Resin (Dentsply/Caulk Div.), followed by light curing each surface for 20 seconds. They were stored in water after 8 minutes.

Group 4. Excess cement was removed with a pointed camel hair brush and the margins brushed with Prime & Bond NT serving as a modeling liquid (Dentsply/Caulk Div.), followed by light curing each surface for 20 s and storage in water after 8 minutes.

Group 5. Excess cement was immediately removed with a rubber tip (periodontal stimulator), subsequently covered with DeOx (Ultradent Products Inc. South Jordan, Utah) to prevent the formation of an oxygen inhibited layer, and the cement light cured for 30 s per surface. After 8 minutes the samples were stored in water.

The dental resin cement used to brush the dental margins after removal of excess cement may be the same as or different from that used to bond the construct to the tooth to be restored, and is preferably, photocurable.

After completion of the cementation procedure all samples were stored for 24 hours in water and then immersed in a dye solution (Methylene blue) for another 24 hours, rinsed and dried and immediately imbedded in acrylic resin. The imbedded teeth were sectioned in a bucco-lingual direction using a diamond blade (Buehler Isomet, Lake Bluff, Ill.). By means of a stereo light microscope (Olympus, Tokyo, Japan) the cross sections were scored for leakage using the following scoring technique: 0=no leakage; 1=die penetration not exceeding 1 mm; and 2=die penetration beyond 1 mm. The leakage scores were tabulated and representative samples photographed. The samples were then prepared for Field Emission Scanning Electron Microscopy (FESEM) (Jeol 6320, Medford, Mass.), coated with gold palladium and observed at 130× magnification at 8 KV. A total of 6 samples were available for FESEM for each group. To avoid shrinkage artifacts, causing gaps in the order of 200 $\mu$m at the preparation cement interface, replicas were made of some samples immediately after sectioning, thus avoiding preparation artifacts.

Although a preferred brush according to the invention is a pointed camel hairbrush, it will be appreciated that any soft brush with bristles similar in flexibility and stiffness to camel hair is within the scope of the invention. By "pointed" it is meant a brush having at least one sharp edge formed by the bristles.

Results

The dye leakage scores and interpretation of the quality of cement adaptation is presented in Table 1. The quality of the adaptation was described as, 1. flush with the preparation and crown margin,
2. under contoured when the cement broke within the crown margin,
3. presence of excess cement was noted,
4. cement surface had an irregular ragged appearance The worst average leakage scores (1.9) were recorded for Group 5 in which excess cement was removed with a rubber tip. For Group 4 in which the cement was removed with a brush and then contoured with the same brush wetted with Prime & Bond NT, the lowest average scores (0.6) were seen.

Differences between each mode of application and between individual application modes for each composite material were analyzed using Mann-Whitney U-test at p<0.05. The statistical analysis revealed that Group 4, in which excess cement was removed with a brush and the margins brushed to contour with Prime & Bond NT used as a modeling liquid, demonstrated significantly less shrinkage than all other groups.

FESEM Interpretation

Representative micrographs are described below.

FIG. 1 is an example of Group 1. Excess cement (EC) extruding bulbously from the margin and measuring ±220 to 330 $\mu$m can be seen at the marginal opening, covering gold casting and tooth. The marginal adaptation measures ±80 $\mu$m. The separation between extruded cement and cement between casting and preparation is an artifact caused by dehydration of the sample.

Figure 2:
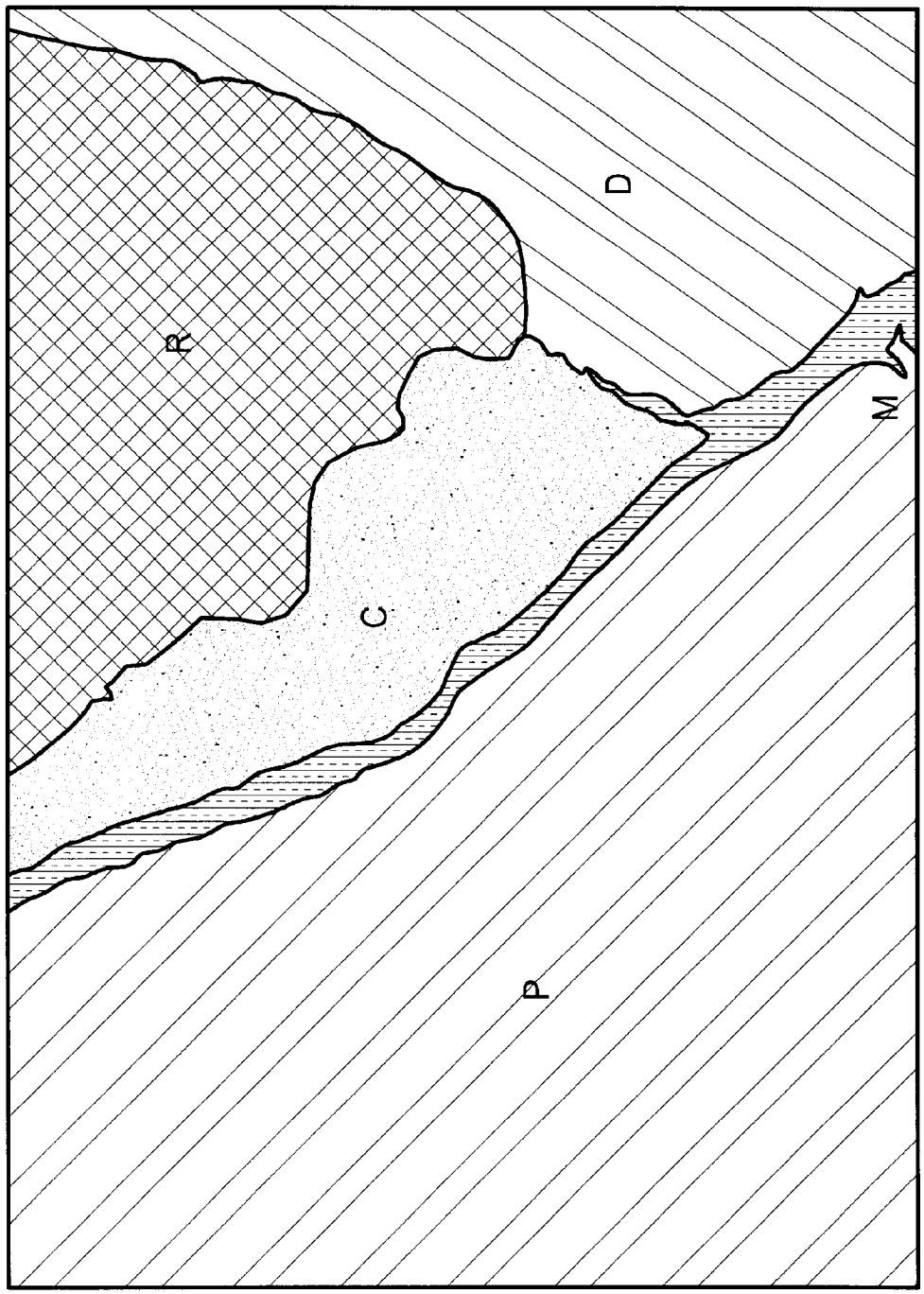
Figure 3:
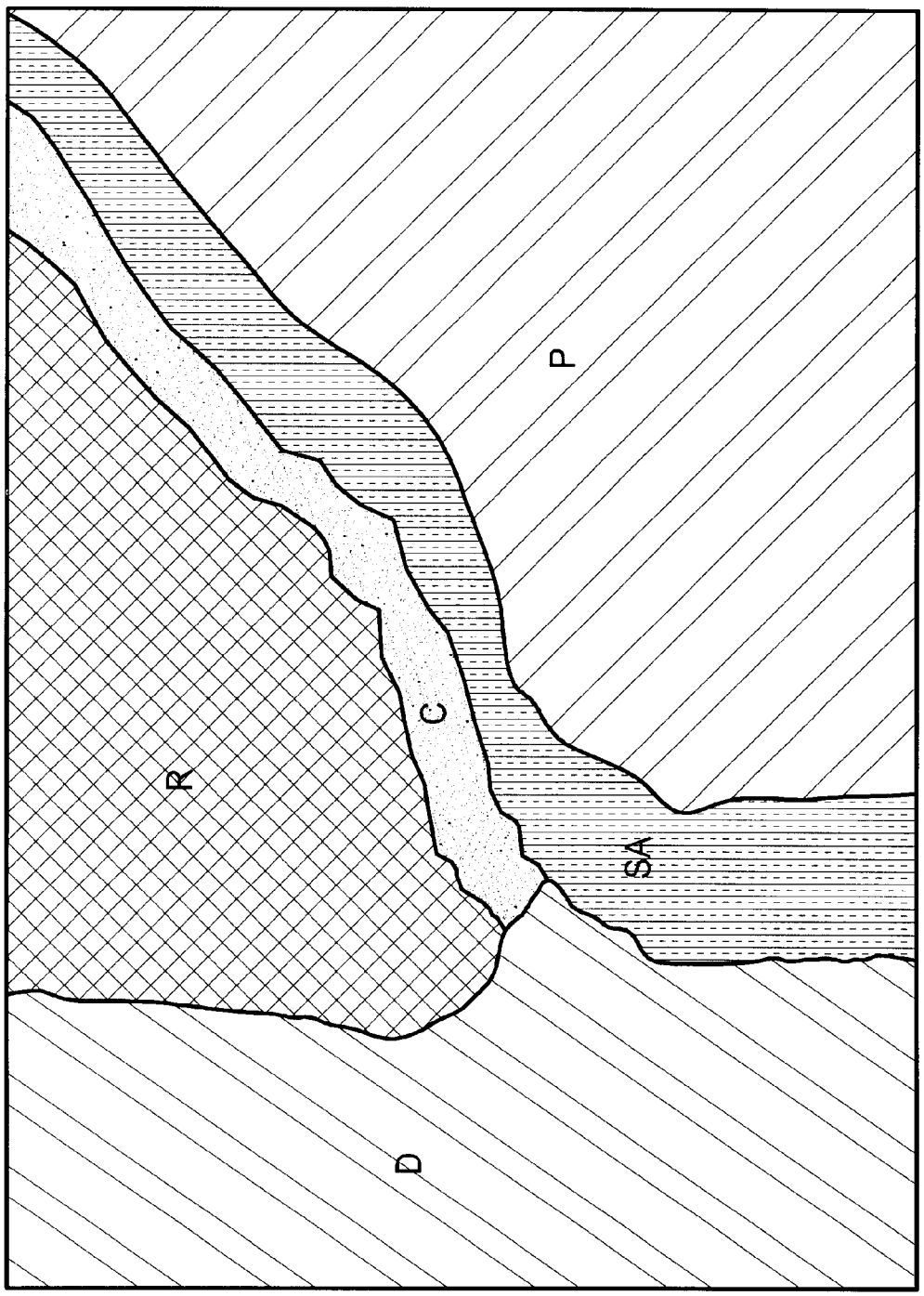
FIG. 3. A FESEM of Group 3. Ignoring the preparation artifact (SA), the cement adaptation was quite good and in the order of <50 m$\mu$. However, the cement does not follow the contour of the preparation (P). The margin extended beyond the contour of the preparation (P). The margin extended beyond the border of the cement.
Figure 4:
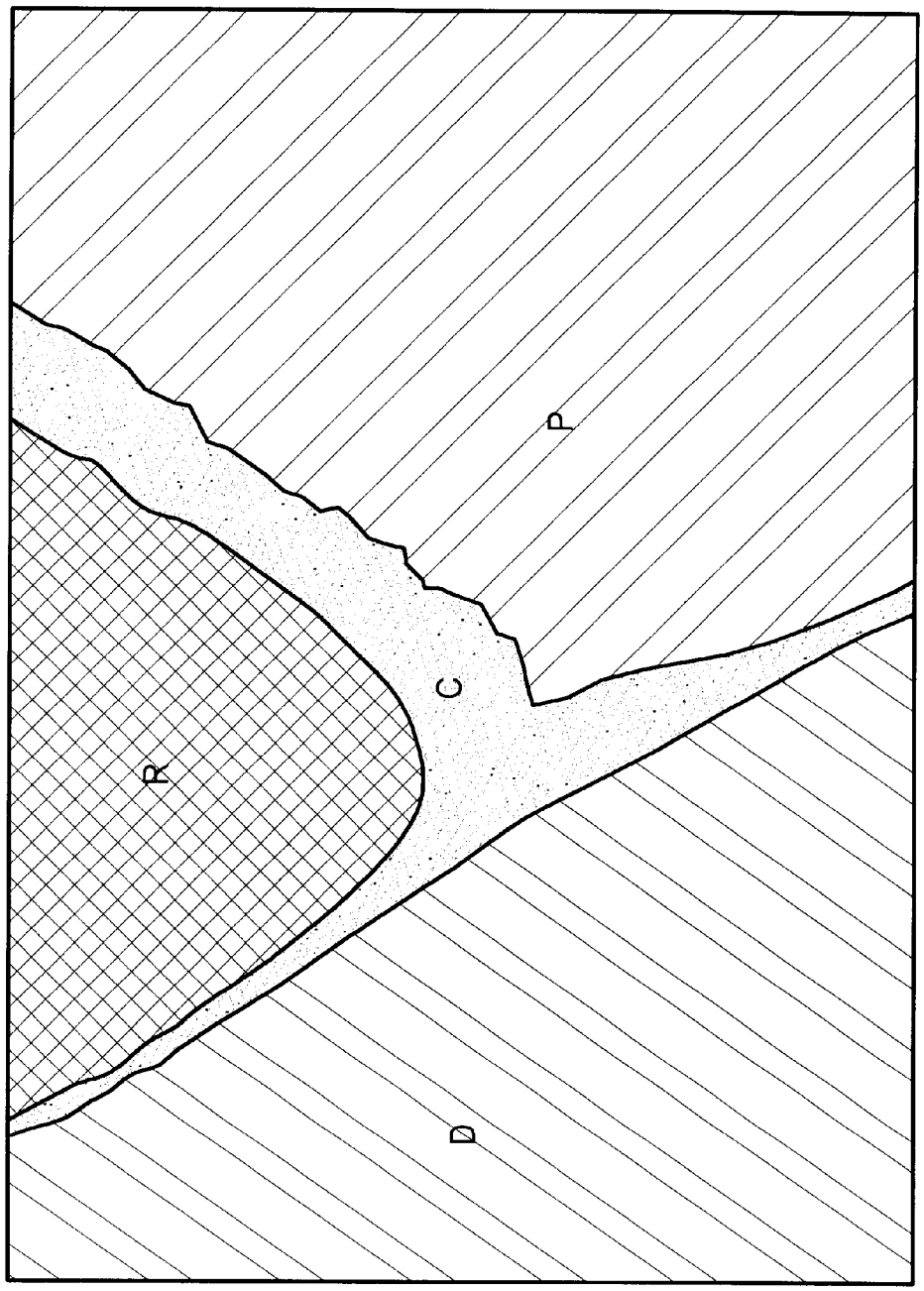
FIG. 4. A FESEM of a replica of a sample of Group 4. The cement (C) is continuous with the emergence profile of the preparation (P) and restoration (R). Note the absence of shrinkage artifacts. The marginal adaptation is ±90 m$\mu$.

FIG. 2 (2-1) shows a cement adaptation short of the actual margin (M) in an amount of 75–100 $\mu$m. FIG. 3 is a micrograph of a sample finished with the technique using Probond Resin as a margin modeling resin. It shows a cement margin that is not continuous with the casting/preparation contour. The space between cement and preparation is a shrinkage artifact. FIG. 4 is a micrograph from a replica of a sample of Group 4. The margin shows a cement adaptation that is continuous with the contour of casting and tooth. Note the absence of the artificial shrinkage gap, which is caused by dehydration of the tooth under vacuum as required for scanning electron microscopy preparation and observation. The replicas were made of the sections before preparation for FESEM. Almost all sections demonstrated this "brushed to contour" feature when Prime & Bond NT was used as a modeling liquid.

The much lower leakage scores for Group 4 were significant compared to all other groups (p≦0.05). Dye penetration revealed a tendency for the least penetration in samples with a continuous margin and the use of a bonding agent as modeling liquid. The range of marginal adaptation of the restorations was from to 100 $\mu$m. A marginal discrepancy of less than 50 $\mu$m and as much as 150 $\mu$m has been suggested as a clinical acceptable opening, for cast restorations. The low viscosity of the bonding agent that was used as a modeling liquid penetrated the interface and sealed the margin. Thus, as an added benefit of providing the best contoured and adapted margins, there was the additional benefit that this technique reduced marginal leakage. It can not be determined from this study whether the use of a bonding agent as modeling liquid, in cases where the acid etch technique and a bonding agent has been used in combination with a resin based or resin ionomer cement for final cementation, would have had an equal positive effect on the marginal seal, since all castings were cemented with a resin cement only.

The importance of well adapted margins of the restoration cannot be overemphasized. A healthy coexistence between dental restorations and the surrounding periodontal structures is a goal of tooth reconstruction. The placement of restorations with overhanging or over contoured subgingival margins can be responsible for changes in the micro flora population and may potentially increase the possibility of gingival inflammation and loss of periodontal ligament attachment. The success of brushing the cement to contour will greatly depend on the quality of the final restoration. Although the unfilled resin in Group 3 produced acceptable margins the material had a too heavy viscosity and did not offer the benefit of reduction in marginal leakage. Apparently there is a risk to break off the cement within the crown margin during the in initial setting reaction, causing a rough and irregular surface. This technique also did not guarantee removal of all cement and frequently left excesses on the restoration and the tooth cervical to the margin. Considering the excess cement that was left behind when using a rubber tip this technique cannot be recommended. It appears that the tip was not pliable enough to follow the contours of the restoration/tooth interface. It is recognized that mostly accessible areas are suitable for the technique in Group 4. Yet, a pointed brush has better access to interproximal surfaces than most other instruments. Of course the use of floss to clean interproximal surfaces is a step that cannot be omitted. The remnants of the luting process must be totally eliminated to provide a perfectly smooth marginal interface that blends seamlessly into a physiologically tolerable emergence profile of tooth/margin/restoration.

The use of applicator brushes for cement removal is strongly discouraged since the stiff bristles have access to the margins "ranking" the cement away causing ditching at the interface, resulting in staining. In the past few years, the use of resin cements has dramatically increased because of the successful results achieved when combining them with ceramic veneers, inlays, onlays and crowns. The adhesive luting techniques are not only for ceramics restorations, however, and can be used for metallic or metal/porcelain restorations as well. Since the quality of the margins are critical to the longevity of cemented dental restorations it was of particular interest to study the most appropriate way to clean and seal these margins. Access for cement removal is an important consideration. In this study, soft hard tissue did not impede access and vision, therefore, it is probable that cement removal was more effective than it would be in vivo. It can be concluded that pointed sable hair brushes should be in the armamentarium of every dentist who uses resin cement for final cementation to clean and contour resin-based cements. In spite of the fact that resin ionomers were not tested we feel that this recommendation also applies to this category of cements since they similar clinical characteristics. Especially the use of a bonding agents serving as "modeling liquid" can improve the quality of the marginal adaptation and reduce marginal leakage.

TABLE 1

Results of the microleakage scores (0 = none; 1 = 1 mm; 2 = >1 mm) and description of the appearance of the cement at the interface casting/preparation.

| Group | Mean Microleakage score | Microscopic features of cement adaptation |
| --- | --- | --- |
| 1 | 1.5 | Flush with margin, broke within margin some excess, large amount of excess |
| 2 | 1.5 | Ragged, cement broke within margin, presence of extruded cement |
| 3 | 1.7 | Flush with margins, slightly irregular, excess |
| 4 | 0.6 | Flush with margins |
| 5 | 1.9 | Open margin, slight extrusion, irregular |

What is claimed is:

1. In a method of restoring a tooth using a dental construct, of the type wherein the construct is placed onto the tooth using a dental cement to bond the construct to the tooth, the improvement comprising:

after placement of the construct onto the tooth, removing excess cement with a soft, pointed brush; brushing the dental margins with a photocurable dental resin cement which is the same as or different from the dental cement used to bond the construct to the tooth; and, light curing the photocurable dental resin cement.

* * * * *